(12) United States Patent
Irvin

(10) Patent No.: US 8,662,480 B1
(45) Date of Patent: Mar. 4, 2014

(54) FAN POWERED AIR FRESHENER AUTOMOBILE POWER OUTLET

(75) Inventor: Aaron Irvin, Salt Lake City, UT (US)

(73) Assignee: American Covers, Inc., Draper, UT (US)

( * ) Notice: Subject to any disclaimer, the term of this patent is extended or adjusted under 35 U.S.C. 154(b) by 349 days.

(21) Appl. No.: 13/281,890

(22) Filed: Oct. 26, 2011

Related U.S. Application Data

(60) Provisional application No. 61/408,220, filed on Oct. 29, 2010.

(51) Int. Cl.
*B01F 3/04* (2006.01)

(52) U.S. Cl.
USPC .......... 261/26; 261/30; 261/DIG. 88; 422/124

(58) Field of Classification Search
USPC .................. 261/26, 30, DIG. 88; 422/124
See application file for complete search history.

(56) References Cited

U.S. PATENT DOCUMENTS

| | | |
|---|---|---|
| D176,671 S | 4/1876 | Myers |
| 369,878 A | 9/1887 | Palmer |
| 1,171,737 A | 2/1916 | Madigan |
| D140,109 S | 1/1945 | Pierce |
| 2,642,248 A | 6/1953 | Semon |
| 2,733,333 A | 1/1956 | Peters |
| D177,826 S | 5/1956 | Katz |
| D178,237 S | 7/1956 | Katz |
| 3,239,145 A | 3/1966 | Aurelio |
| 3,456,106 A | 7/1969 | Gluschkin Mischa |
| 3,655,129 A | 4/1972 | Seiner |
| 3,847,305 A | 11/1974 | Tobin |
| 3,948,445 A | 4/1976 | Andeweg |
| 3,971,858 A | 7/1976 | Collier et al. |
| D246,986 S | 1/1978 | Costello |
| 4,084,079 A | 4/1978 | Costello |
| D250,041 S | 10/1978 | Schimanski |
| 4,149,675 A | 4/1979 | Van Breen et al. |
| 4,184,099 A | 1/1980 | Lindauer et al. |
| 4,226,944 A | 10/1980 | Stone et al. |
| D258,511 S | 3/1981 | Ashton |

(Continued)

FOREIGN PATENT DOCUMENTS

| | | |
|---|---|---|
| CA | 2077251 | 5/1993 |
| EP | 0 348 970 | 1/1990 |

(Continued)

OTHER PUBLICATIONS

About.Com Housekeeping, http://housekeeping.about.com/od/pr . . . affresh, Febrezee Noticeables, accessed Oct. 2, 2008, 2 pages.

(Continued)

*Primary Examiner* — Robert A Hopkins
(74) *Attorney, Agent, or Firm* — Thorpe North & Western LLP

(57) ABSTRACT

An air freshener includes a housing with a stem and a head with a cavity therein. An air displacement mechanism is carried by the housing and includes a rotatable fan carried by the head, and a motor coupled to the fan to rotate the fan. A scent capsule is removably carried by the head and has a chamber containing a fragrant material and a permeable membrane through which a fragrance of the fragrant material can permeate over time. The permeable membrane is located adjacent the fan.

20 Claims, 10 Drawing Sheets

(56) References Cited

U.S. PATENT DOCUMENTS

| | | |
|---|---|---|
| 4,280,649 A | 7/1981 | Montealegre |
| 4,301,949 A | 11/1981 | Palson et al. |
| 1,683,545 A | 9/1982 | Harris |
| 4,382,548 A | 5/1983 | Van der Heijden |
| 4,391,781 A | 7/1983 | Van Lit |
| 4,517,326 A | 5/1985 | Cordts et al. |
| 4,549,693 A | 10/1985 | Barlics |
| 4,594,380 A | 6/1986 | Chapin et al. |
| D286,323 S | 10/1986 | Haworth |
| 4,638,057 A | 1/1987 | Takahashi et al. |
| 4,649,046 A | 3/1987 | Kross |
| 4,703,070 A | 10/1987 | Locko et al. |
| RE32,834 E | 1/1989 | Cordts et al. |
| 4,808,347 A | 2/1989 | Dawn |
| 4,840,773 A | 6/1989 | Wade |
| 4,849,606 A | 7/1989 | Martens et al. |
| 4,874,129 A | 10/1989 | DiSapio et al. |
| 4,880,690 A | 11/1989 | Szycher et al. |
| 4,950,542 A | 8/1990 | Barker |
| 4,968,456 A | 11/1990 | Muderlak et al. |
| 5,008,115 A | 4/1991 | Lee et al. |
| 5,019,434 A | 5/1991 | Matsumoto |
| 5,034,222 A | 7/1991 | Kellett et al. |
| D319,781 S | 9/1991 | Halm et al. |
| 5,050,798 A | 9/1991 | Sulivan |
| D322,558 S | 12/1991 | Halm et al. |
| 5,071,704 A | 12/1991 | Fischel-Ghodsian |
| 5,114,625 A | 5/1992 | Gibson |
| 5,120,583 A | 6/1992 | Garcia |
| 5,178,327 A | 1/1993 | Palamand et al. |
| 5,180,107 A | 1/1993 | Lindauer |
| 5,193,445 A | 3/1993 | Ferguson |
| D334,975 S | 4/1993 | Bunce |
| 5,220,636 A | 6/1993 | Chang |
| D338,519 S | 8/1993 | Peterson |
| 5,234,162 A | 8/1993 | Sullivan |
| 5,240,487 A | 8/1993 | Kung |
| D349,157 S | 7/1994 | Rymer |
| D350,192 S | 8/1994 | Patel et al. |
| 5,368,822 A | 11/1994 | McNeil |
| 5,407,642 A | 4/1995 | Lord |
| D367,526 S | 2/1996 | Bignon |
| D367,924 S | 3/1996 | Patel et al. |
| 5,520,921 A | 5/1996 | Chalifoux |
| D373,626 S | 9/1996 | Dente et al. |
| D375,350 S | 11/1996 | Patel et al. |
| 5,595,194 A | 1/1997 | Talbot |
| D380,258 S | 6/1997 | Muller et al. |
| 5,651,522 A | 7/1997 | Davis et al. |
| 5,683,285 A | 11/1997 | Wong |
| 5,695,692 A | 12/1997 | Kennedy |
| 5,704,832 A | 1/1998 | Borrell |
| D390,941 S | 2/1998 | Cessaroni et al. |
| D392,032 S | 3/1998 | Zaragoza et al. |
| 5,762,549 A | 6/1998 | Scheuer et al. |
| 5,780,527 A | 7/1998 | O'Leary |
| 2,794,767 A | 8/1998 | Wilson |
| 5,820,791 A | 10/1998 | Canale |
| D400,662 S | 11/1998 | Davis |
| 5,845,847 A | 12/1998 | Martin et al. |
| 5,860,552 A | 1/1999 | Culhane et al. |
| 5,861,128 A | 1/1999 | Vick et al. |
| D404,957 S | 2/1999 | Cheris et al. |
| 5,871,765 A | 2/1999 | Johnson et al. |
| D410,540 S | 6/1999 | Pinchuk |
| D411,002 S | 6/1999 | Farmer |
| D415,267 S | 10/1999 | Kauzlarich et al. |
| D415,268 S | 10/1999 | Farmer |
| 5,988,520 A | 11/1999 | Bitner |
| D417,727 S | 12/1999 | Christianson |
| 6,044,202 A | 3/2000 | Junkel |
| D424,677 S | 5/2000 | Chen |
| D425,190 S | 5/2000 | Morikawa |
| 6,111,055 A | 8/2000 | Berger et al. |
| 6,123,906 A | 9/2000 | Farmer |
| 6,123,935 A | 9/2000 | Wefler et al. |
| D432,222 S | 10/2000 | Rymer et al. |
| D435,694 S | 12/2000 | Lebherz |
| D437,038 S | 1/2001 | Chuan |
| 6,190,607 B1 | 2/2001 | Farmer |
| 6,191,197 B1 | 2/2001 | Wang et al. |
| 6,202,938 B1 | 3/2001 | Collier |
| D440,294 S | 4/2001 | Bilek |
| D441,441 S | 5/2001 | Upson |
| 6,264,887 B1 | 7/2001 | Farmer |
| 6,291,371 B1 | 9/2001 | Shefer et al. |
| 6,309,715 B1 | 10/2001 | Lindauer et al. |
| 6,325,475 B1 | 12/2001 | Hayes et al. |
| D454,190 S | 3/2002 | Trocola |
| 6,357,260 B1 | 3/2002 | Lutz |
| 6,374,044 B1 | 4/2002 | Freidel |
| 6,375,966 B1 | 4/2002 | Maleeny et al. |
| 6,379,689 B1 | 4/2002 | Aguadisch |
| 6,416,043 B1 | 7/2002 | Eisenbraun |
| 6,514,467 B1 | 2/2003 | Bulsink et al. |
| D472,968 S | 4/2003 | Christianson |
| D478,379 S | 8/2003 | Talenton et al. |
| D478,973 S | 8/2003 | Wagner |
| D479,592 S | 9/2003 | Lammel et al. |
| D485,343 S | 1/2004 | Wu |
| D487,504 S | 3/2004 | Yuen |
| 6,712,286 B2 | 3/2004 | Baxter et al. |
| D488,214 S | 4/2004 | Quantin |
| D488,548 S | 4/2004 | Lablaine |
| D491,257 S | 6/2004 | Picken |
| D491,798 S | 6/2004 | Buthier |
| D496,720 S | 9/2004 | Dudley |
| 6,800,252 B1 | 10/2004 | Jedzinski |
| 6,885,811 B2 | 4/2005 | He et al. |
| D504,943 S | 5/2005 | Dudley |
| D507,341 S | 7/2005 | Taylor |
| D511,568 S | 11/2005 | Wheatley |
| D514,679 S | 2/2006 | Wheatley |
| D515,192 S | 2/2006 | Smith et al. |
| 7,025,283 B2 | 4/2006 | Torres |
| 7,055,764 B1 | 6/2006 | Martinez et al. |
| 7,061,386 B2 | 6/2006 | Seresini |
| 7,137,570 B2 | 11/2006 | Wheatley et al. |
| D535,376 S | 1/2007 | Michaels et al. |
| D535,379 S | 1/2007 | Hundertmark |
| 7,159,792 B2 | 1/2007 | Wheatley et al. |
| D544,080 S | 6/2007 | Carlson |
| D544,084 S | 6/2007 | Michaels et al. |
| D544,594 S | 6/2007 | Zobele |
| D544,953 S | 6/2007 | Kee |
| D546,432 S | 7/2007 | Hundertmark |
| 7,243,859 B2 | 7/2007 | Caserta et al. |
| D548,317 S | 8/2007 | Newton et al. |
| D550,345 S | 9/2007 | Weggelaar |
| D551,333 S | 9/2007 | Wu |
| 7,285,248 B2 | 10/2007 | Yamamoto et al. |
| D554,746 S | 11/2007 | Davis et al. |
| 7,293,719 B2 | 11/2007 | Wheatley et al. |
| D565,162 S | 3/2008 | Carlson |
| 7,344,123 B2 | 3/2008 | Pankhurst et al. |
| D565,715 S | 4/2008 | Wu |
| D573,706 S | 7/2008 | Zlotnik et al. |
| D574,941 S | 8/2008 | Weggelaar |
| 7,441,360 B2 | 10/2008 | Christianson et al. |
| D580,039 S | 11/2008 | Zlotnik et al. |
| D585,129 S | 1/2009 | Huang |
| D585,971 S | 2/2009 | Carrizales |
| D591,415 S | 4/2009 | Wu |
| D593,670 S | 6/2009 | Valentiono et al. |
| D594,953 S | 6/2009 | King et al. |
| D594,954 S | 6/2009 | Wheatley |
| 7,544,332 B2 | 6/2009 | De Silva et al. |
| D597,645 S | 8/2009 | Thompson |
| D598,531 S | 8/2009 | Irvin |
| D607,983 S | 1/2010 | Irvin |
| 7,651,666 B2 | 1/2010 | Adair et al. |
| 7,670,566 B2 | 3/2010 | Adair et al. |
| 7,687,037 B2 | 3/2010 | Wheatley et al. |
| 7,687,038 B2 | 3/2010 | Wheatley |

(56) References Cited

U.S. PATENT DOCUMENTS

| | | | |
|---|---|---|---|
| D614,277 S | 4/2010 | Hsiao | |
| D619,692 S | 7/2010 | Hami et al. | |
| D619,693 S | 7/2010 | Hami et al. | |
| D619,694 S | 7/2010 | Hami et al. | |
| D620,573 S | 7/2010 | Hami et al. | |
| D622,835 S | 8/2010 | Mendheim | |
| 7,780,094 B2 | 8/2010 | Caserta et al. | |
| D625,798 S | 10/2010 | Hami et al. | |
| D629,881 S | 12/2010 | Valentino et al. | |
| D631,534 S | 1/2011 | Kajizuka | |
| D631,954 S | 2/2011 | Bertassi et al. | |
| D633,610 S | 3/2011 | Wu | |
| D637,275 S | 5/2011 | Baraky | |
| D640,358 S | 6/2011 | Irvin | |
| D642,668 S | 8/2011 | Lablaine | |
| D645,949 S | 9/2011 | Brandenburg et al. | |
| D647,186 S | 10/2011 | Chan et al. | |
| D649,237 S | 11/2011 | Bilko et al. | |
| D650,892 S | 12/2011 | Wheatley | |
| D662,581 S | 6/2012 | Savengnago | |
| 8,197,761 B1 * | 6/2012 | Miller-Larry | 422/125 |
| 8,485,454 B1 | 7/2013 | Irvin | |
| 8,490,846 B1 | 7/2013 | Wheatley | |
| 2003/0097936 A1 | 5/2003 | Maleeny et al. | |
| 2003/0199421 A1 | 10/2003 | Copfer | |
| 2004/0265164 A1 | 12/2004 | Woo et al. | |
| 2005/0127538 A1 | 6/2005 | Fabrega et al. | |
| 2005/0169793 A1 | 8/2005 | Wheatley et al. | |
| 2006/0043216 A1 | 3/2006 | Robinson | |
| 2006/0078477 A1 | 4/2006 | Althouse et al. | |
| 2006/0279008 A1 | 12/2006 | Jursich | |
| 2007/0057084 A1 | 3/2007 | Vieira | |
| 2007/0160492 A1 | 7/2007 | Spector | |
| 2007/0290064 A1 | 12/2007 | Majerowski et al. | |
| 2008/0099576 A1 | 5/2008 | Hart | |
| 2008/0128925 A1 | 6/2008 | Pankhurst et al. | |
| 2009/0008411 A1 | 1/2009 | Schumacher et al. | |
| 2009/0010813 A1 | 1/2009 | Wang et al. | |
| 2009/0173799 A1 | 7/2009 | Litten-Brown et al. | |
| 2010/0010409 A1 | 1/2010 | Irvin | |
| 2010/0019059 A1 | 1/2010 | Bulsink et al. | |
| 2010/0065654 A1 | 3/2010 | Wheatley et al. | |
| 2010/0187327 A1 | 7/2010 | Irvin | |
| 2011/0110823 A1 | 5/2011 | Wheatley | |

FOREIGN PATENT DOCUMENTS

| | | |
|---|---|---|
| EP | 1 346 734 | 9/2003 |
| WO | WO 98/46284 | 10/1998 |
| WO | WO 00/24434 | 5/2000 |
| WO | WO 00/64498 | 11/2000 |
| WO | WO 02/35975 | 5/2002 |
| WO | WO 02/38029 | 5/2002 |
| WO | WO 2006/010282 | 2/2006 |
| WO | WO 2006/084160 | 8/2006 |
| WO | WO 2004/078219 | 1/2007 |
| ZA | 20004637 | 9/2000 |

OTHER PUBLICATIONS

Aromate E-News, Innovation in Novelty Fragrance, Http://209.85. 173.104/seasrch?qcach . . ., accessed Oct. 8, 2008, 2 pages.
ecrater, www.ecrater.com/product.hp?. . ., Yankee Candle Selects Two Scents Electric Fragrance Unit Macintosh/Home Sweet Home, accessed Oct. 2, 2008, 1 page.
http://decomodo.com/articles/categor/lighting/, Bamboo Pillar Candle, Jan. 8, 2008, 1 page.
http://shop.advanceautoparts.com/webapp/wcs/stores/servlet/product_6170795-P_N3004 . . .Advance Auto Part; Arometrics Dual-Scent Vent—Juicy Strawberry and Vanilla; 1 Page; accessed Dec. 10, 2010.
http://www.bestliquidations.com/Medo_Vent Frehser.htm; BestLiquidations.com; Medo Vent Fresh Air Fresheners; 2 pages; accessed Dec. 10, 2010.
Medo® Air Fresheners; Auto Expressions™ 2005 Product Catalog; 25 pages.
Pictures (3) of Medo® auto Expressions Vent™ Air Freshener distributed by SOPUS Products of Moorpark , CA 2003 copyright date on package.
Scents & Sprays, www.scentsandsprays.com/ya . . ., Yankee Autumn Bounty Electric 2 Home Air Fresheners, copyright 2001-2008 scentsandsprays.com, accessed Oct. 2, 2008, 1 page.
U.S. Appl. No. 13/191,966, filed Jul. 27, 2011; Aaron Irvin.
U.S. Appl. No. 12/378,121, filed Oct. 29, 2010; Aaron Irvin.
U.S. Appl. No. 12/915,924, filed Oct. 29, 2010; Nathaniel Finlay.
U.S. Appl. No. 12/915,983, filed Oct. 29, 2010; Alan J. Wheatley.
U.S. Appl. No. 12/916,038, filed Oct. 29, 2010; Aaron Irvin.
U.S. Appl. No. 12/979,763, filed Dec. 28, 2010; Aaron Irvin.
U.S. Appl. No. 12/979,795, filed Dec. 28, 2010; Aaron Irvin.
U.S. Appl. No. 12/979,813, filed Dec. 28, 2010; Aaron Irvin.
U.S. Appl. No. 29/378,112, filed Oct. 29, 2010; Nathaniel Finlay.
www.4imprint.com/EXEC/DETAIL/FROMPRODUCTGROUP/ ~SKU100300/~CA100300.htm, Hot Rod Vent Stick Air Freshner (it . . ., accessed Aug. 12, 2008, 2 pages.
www.autothing.com/Products/Air%20Fresheners/air%20freshener-clip.htm, Air Fresheners, Fresh Scents for you mobile Life, Clip-on Air Vent Clips rom Eagle o., Accessed Aug. 12, 2008, 1 page.
www.chicscents.com/Products.aspx Island Adventure Sandals; 2 pages; accessed Feb. 1, 2011.
www.chicscents.com/Products.aspx; Inspiration 3-D by Chic; 2 pages; accessed Feb. 1, 2011.
U.S. Appl. No. 13/282,035, filed Oct. 26, 2011; Nathaniel Finlay.
U.S. Appl. No. 13/359,726, filed Jan. 27, 2012; Aaron Irvin.
U.S. Appl. No. 12/979,763, filed Dec. 28, 2010; Aaron Irvin; office action dated Dec. 14, 2012.
U.S. Appl. No. 12/693,543, filed Jan. 26, 2010; Aaron Irvin; office action dated Dec. 18, 2012.
U.S. Appl. No. 12/979,795, filed Dec. 28, 2010; Aaron Irvin; office action dated Jan. 28, 2013.
U.S. Appl. No. 13/009,574, filed Jan. 19, 2011; Alan J. Wheatley; office action dated Jan. 11, 2013.
U.S. Appl. No. 12/979,813, filed Dec. 28, 2010; Aaron Irvin; office action dated Jan. 31, 2013.
U.S. Appl. No. 12/915,983, filed Oct. 29, 2010; Alan J. Wheatley; notice of allowance dated Feb. 20, 2013.
U.S. Appl. No. 29/435,389, filed Oct. 23, 2012; Aaron Irvin; notice of allowance dated Mar. 1, 2013.
U.S. Appl. No. 12/979,601, filed Dec. 28, 2010; Alan J. Wheatley; office action dated Mar. 1, 2013.
U.S. Appl. No. 13/009,574, filed Jan. 19, 2011; Alan J. Wheatley notice of allowance dated Apr. 3, 2013.
U.S. Appl. No. 13/359,726, filed Jan. 27, 2012; Aaron Irvin; office action dated Apr. 5, 2013.
U.S. Appl. No. 12/979,763, filed Dec. 28, 2010; Aaron Irvin; noticed of allowance dated Apr. 15, 2013.
U.S. Appl. No. 29/415,358, filed Mar. 9, 2012; Aaron Irvin; Notice of Allowance issued May 29, 2012.
U.S. Appl. No. 12/693,543, filed Jan. 26, 2010; Aaron Irvin; office action dated Aug. 7, 2012.
U.S. Appl. No. 12/979,795, filed Dec. 28, 2010; Aaron Irvin; office action dated Sep. 13, 2012.
U.S. Appl. No. 12/979,813, filed Dec. 28, 2010; Aaron Irvin, office action dated Sep. 14, 2012.
U.S. Appl. No. 29/435,391, filed Oct. 23, 2012; Aaron Irvin; notice of allow dated Jun. 18, 2013.
U.S. Appl. No. 13/282,035, filed Oct. 26, 2011; Nathaniel Finlay; office action dated Jul. 17, 2013.

* cited by examiner

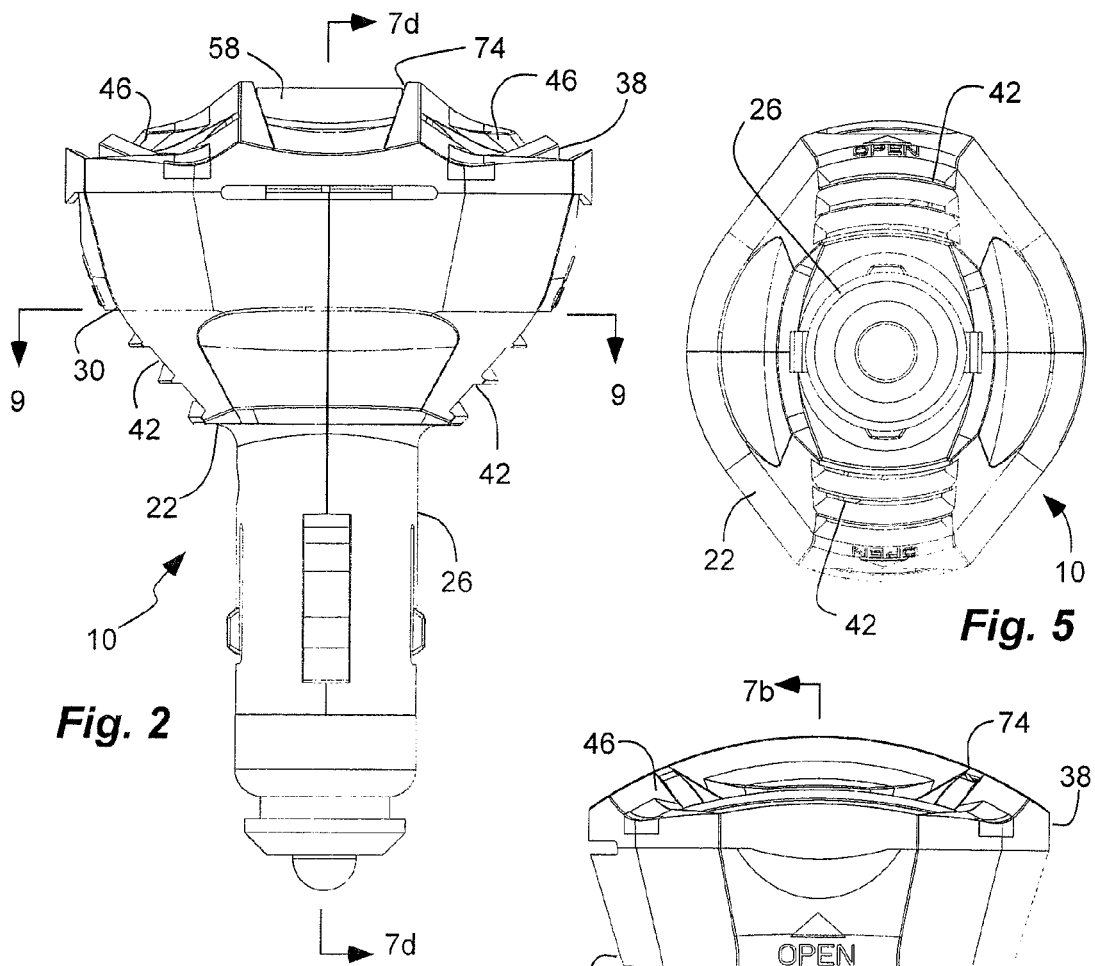
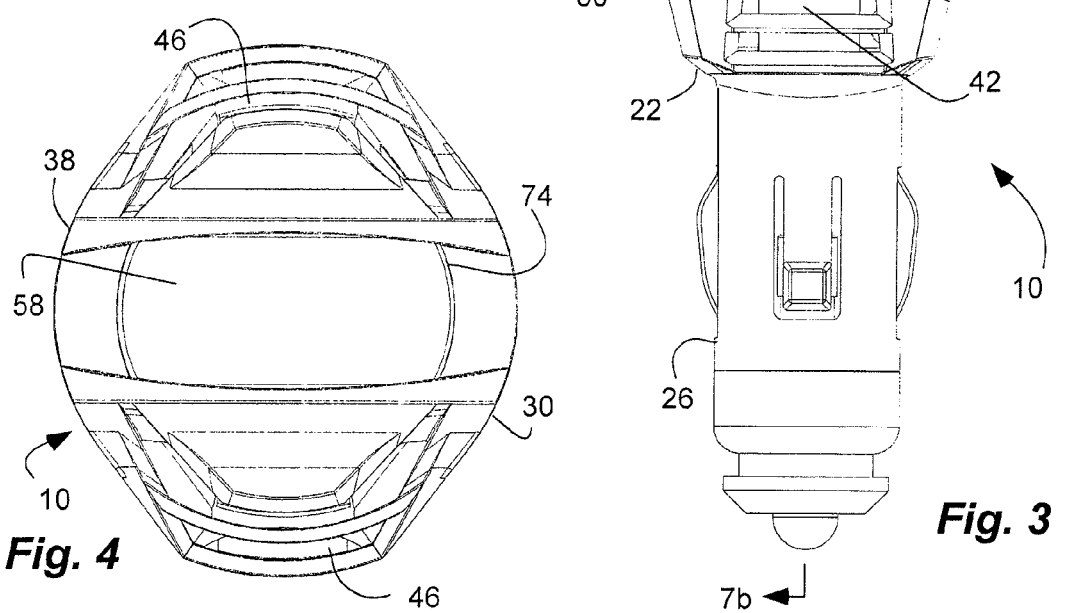
Fig. 2
Fig. 5
Fig. 3
Fig. 4

FAN POWERED AIR FRESHENER AUTOMOBILE POWER OUTLET

CROSS-REFERENCE TO RELATED APPLICATIONS AND CLAIM OF PRIORITY

Priority of U.S. Provisional Patent Application Ser. No. 61/408,220, filed on Oct. 29, 2010, is claimed, and is herein incorporated by reference.

BACKGROUND

1. Field of the Invention

The present invention relates generally to air fresheners.

2. Related Art

Automobile fan driven air fresheners have been proposed. See, for example, U.S. Pat. Nos. 4,968,456 and 4,808,347. Other air fresheners include a light source. See, for example, U.S. Pat. Nos. 7,293,719 and 7,687,037.

SUMMARY OF THE INVENTION

It has been recognized that it would be advantageous to develop an air freshener to provide a desired scent or neutralizing agent for use with a power outlet of an automobile.

The invention provides an air freshener configured to be carried by a power outlet of an automobile. The air freshener includes a housing with a stem and a head with a cavity therein. The stem is sized and shaped to be inserted into the power outlet of the automobile. An air displacement mechanism is carried by the housing and includes a rotatable fan carried by the head, and a motor coupled to the fan to rotate the fan. A scent capsule is removably carried by the head and has a chamber containing a fragrant material and has a permeable membrane through which a fragrance of the fragrant material can permeate over time. The permeable membrane is located adjacent the fan.

In addition, the invention provides an air freshener in combination with a power outlet of an automobile. The air freshener includes a housing with a stem and a bulbous head with a cavity therein. The stem is sized and shaped to be inserted into the power outlet of the automobile, and includes a pair of terminals thereon capable of contacting mating terminals in the power outlet. A cap is disposed on the housing and forms a portion of the bulbous head and the cavity. The bulbous head has a bottom vent aperture in a bottom and a top vent aperture in a top or the cap. An air displacement mechanism is carried by the housing and includes a rotatable fan carried by the bulbous head, and a motor coupled to the fan to rotate the fan. The motor is coupled to the pair of terminals to power the motor. A scent capsule is removably carried by the bulbous head and has a chamber containing a fragrant material and has a substantially flat permeable membrane through which a fragrance of the fragrant material can permeate over time. The permeable membrane located adjacent the fan. An air flow path is defined through bulbous head of the housing in through the bottom vent aperture, past the permeable membrane of the scent capsule, and out of the top vent aperture. The cap includes a scent capsule aperture and the scent capsule includes a clear dome projecting at least to the scent capsule aperture with the fragrant material visible through the clear dome and the scent capsule aperture.

Furthermore, the invention provides an air freshener configured to be carried by a power outlet of an automobile. The air freshener includes a housing with a stem and a bulbous head with a cavity therein. The stem is sized and shaped to be inserted into the power outlet of the automobile, and includes a pair of terminals thereon capable of contacting mating terminals in the power outlet. A cap is disposed on the housing and forms a portion of the bulbous head and the cavity. The bulbous head has a bottom vent aperture in a bottom and a top vent aperture in a top or the cap. An air displacement mechanism is carried by the housing and includes a rotatable fan carried by the bulbous head, and a motor coupled to the fan to rotate the fan. The motor is coupled to the pair of terminals to power the motor. A scent capsule is removably carried by the bulbous head and has a vessel containing a fragrant liquid and is covered by a substantially flat permeable membrane through which a fragrance of the fragrant liquid can permeate over time. The permeable membrane is located adjacent to and facing towards the fan, and is oriented perpendicular to an axis of the fan. The scent capsule has a long dimension oriented transverse to a long dimension of the head with the bottom vent opening and the top vent opening located outside a width of the scent capsule. An air flow path is defined through bulbous head of the housing in through the bottom vent aperture, past the permeable membrane of the scent capsule, and out of the top vent aperture. A scent capsule aperture is formed in the cap. A clear dome of the scent capsule projects at least to the scent capsule aperture, with the fragrant liquid visible through the clear dome and the scent capsule aperture. The membrane is at least translucent. A light source is disposed in the housing to illuminate the membrane and fragrant liquid therein such that light from the light source is visible through the clear dome and the scent capsule aperture.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein:

FIG. 2 is a side view of the air freshener of FIG. 1;

FIG. 3 is a front view of the air freshener of FIG. 1;

FIG. 4 is a top view of the air freshener of FIG. 1;

FIG. 5 is a bottom view of the air freshener of FIG. 1;

Figure 1:
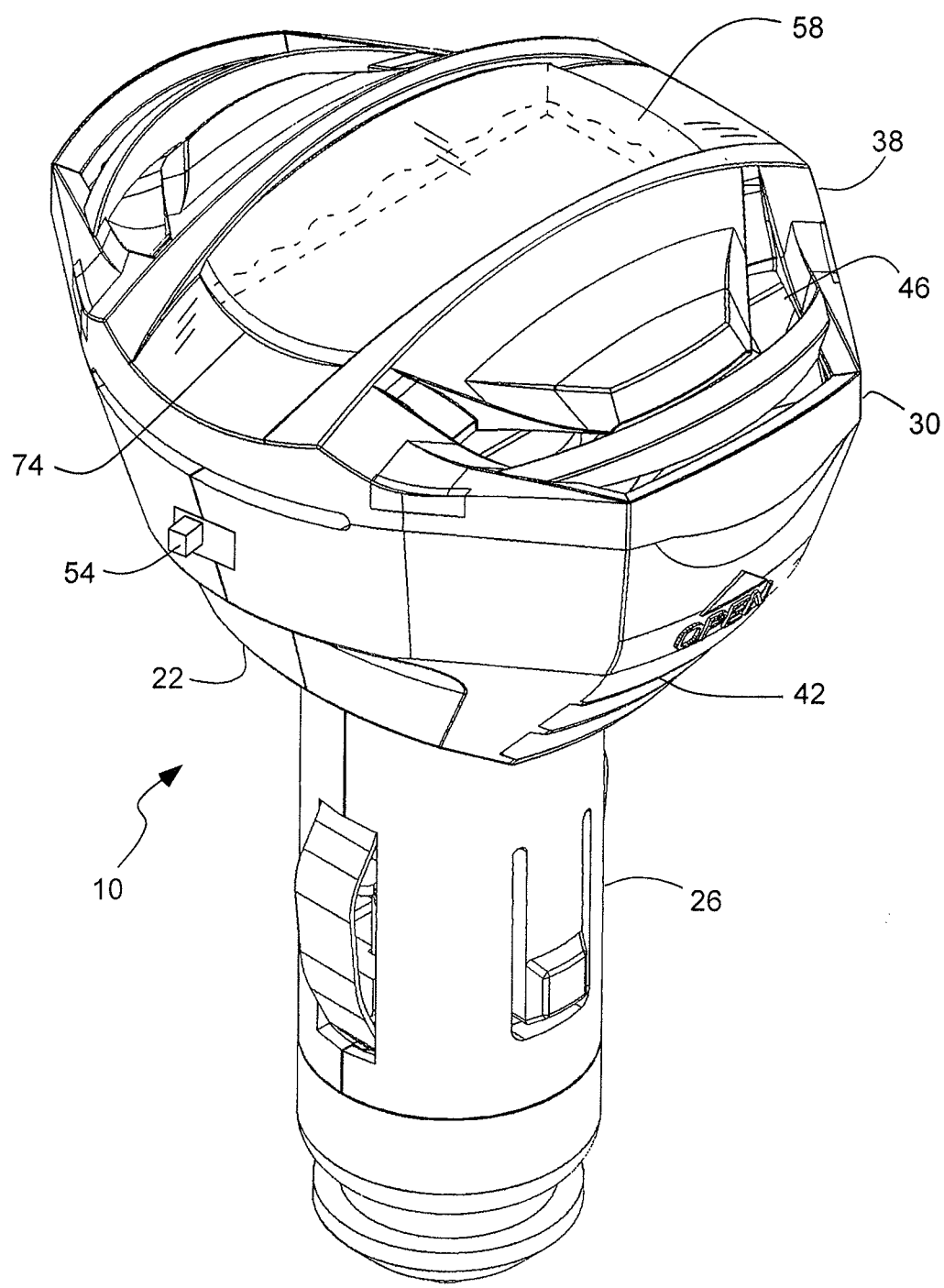
FIG. 1 is a perspective view of an air freshener in accordance with one embodiment of the present invention.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "power outlet" or "power outlet of an automobile or vehicle" is used herein to refer to any type of power outlet available in an automobile or vehicle, and which is typically a 12 volt outlet configured in the style to receive a cigarette lighter or other accessory. Such a power outlet can be located in a dash or console of a vehicle. Such a power outlet may also include an adapter inserted into the power outlet. Such a power outlet can be oriented horizontally, vertically, or at an incline.

The terms "top" and "bottom" and "downwardly" and "upwardly" and the like are used herein relative to the air freshener device or housing thereof being oriented upright or vertical; while it is understood that the device or housing can be oriented horizontally or at an incline during use depending on the orientation of the power outlet.

The term "scent material" and "fragrant material" are used interchangeably herein to refer broadly to a material that carries a desired fragrance or scent, or even a neutralizing agent.

The term "clear dome" is used herein to refer to a dome that is clear or transparent, or that is at least translucent.

DESCRIPTION

As illustrated in FIGS. 1-9, an air freshener device, indicated generally at 10, in an example implementation in accordance with the invention is shown for use with a power outlet of an automobile or vehicle, such as a 12 volt power outlet. Such an outlet is a power outlet for an accessory or cigarette lighter, and is often located in a dash or console of a vehicle. The air freshener can use power from the vehicle to power a fan to disperse a fragrance, etc. The air freshener can provide a desired and/or aesthetically pleasing scent, fragrance, aroma or neutralizing agent. Air fresheners are one example of a field that can benefit from the present invention.

The air freshener 10 includes a housing 22 with a stem 26 and a bulbous head 30 with a cavity 34 therein. The stem can protrude downwardly when vertically oriented and/or with respect to a vertically oriented power outlet, and inwardly into the outlet; while the bulbous head can face or protrude upward when vertically oriented and/or with respect to a vertically oriented power outlet, and outward from the outlet. It will be appreciated that downward and upward are relative to one another base on the orientation of the power outlet, which can face upward, laterally outward (substantially horizontally), or at an incline. The 26 stem can be removably coupled to the outlet so that the air freshener can be inserted as a retrofit accessory, and withdrawn as desired. The stem 26 is sized and shaped to be inserted into the power outlet, such as a 12 volt outlet, of the automobile, and includes a pair of terminals thereon capable of contacting mating terminals in the power outlet. The pair of terminals can include a bottom tip terminal and one or more lateral terminals, corresponding to a bottom terminal and one or more lateral terminals in the power outlet. The head 30 can be bulbous and/or oblong, with a diameter or lateral dimension (width and/or depth) greater than the stem. In addition, the head and the stem can be rigid and/or fixed with respect to one another. Alternatively, the head and the stem can be pivotally coupled together so that the head can pivot to a different orientation despite the orientation of the power outlet. In addition, the head and the stem can be flexible coupled together so that the head can be both pivoted and displaced with respect to the stem and the power outlet.

A cap 38 or cover can be disposed on the housing 22 and/or the head 30, and can form a portion of the bulbous head 30 and the cavity 34. The cap can form a top of the housing and/or head and can span the shape of the head. Thus, the cap can have an oblong shape with a width or lateral dimension greater than a depth (or front to back direction). The cap 38 can be removably coupled to the housing and/or the head to allow removal, insertion and/or replacement of a scent capsule, as described below. The bulbous head 30 of the housing 22 has a bottom vent aperture(s) 42 in a bottom, and a top vent aperture(s) 46 in a top or the cap 38. The vent apertures can be formed on both sides of the bulbous head or housing, and can include a plurality of apertures or louvers. The bottom vent apertures 42 or louvers can face downwardly and laterally outwardly (or inwardly towards the outlet). The top vent apertures 46 can face upwardly (or outwardly away from the outlet and dash or consol). The housing can be formed of plastic and by injection molding, and can include a pair of housing halves coupled together. The cap can be formed of plastic and by injection molding, and can span the housing halves.

An air displacement mechanism is carried by the housing 22 and/or bulbous head 30, and disposed in the cavity 34. The air displacement mechanism can include a rotatable fan 50 or turbine, a motor 52 coupled to the fan to rotate the fan, and the motor coupled to the pair of terminals to power the motor. The fan can be an axial-flow fan with blades, such as propeller style blades, that force air to move parallel to the shaft about which the blades rotate. Alternatively, the fan can be a centrifugal fan with an impeller carrying blades and blowing air at a right angle to the intake of the fan. Alternatively, the fan can be a cross-flow or tangential fan. The housing 22 can include a motor mount or brace 53 (FIG. 8) between the fan and motor and coupled to the housing. The motor or a portion thereof can nest in the stem with an opposite end or shaft held by the motor mount or brace.

The air displacement mechanism can further include a manual switch 54 electrically coupled between the motor and the pair of terminals to selectively activate and deactivate the air displacement mechanism. The switch can be any type of switch, including a slide type switch, a push button type switch, etc. A timer circuit 55 (FIG. 9) can be coupled to the switch to deactivate the fan or the turbine after a predetermined amount of time. Alternatively, the housing, or stem, can be inserted and withdrawn from the power outlet to activate and deactive the air freshener. The air freshener can include control electronics on a printed circuit board disposed in the housing and electrically coupled to the pair of contacts, the motor, the switch and/or the lights, etc.

A scent capsule 58 can be removably carried by the bulbous head 30 of the housing. The scent capsule 58 can be disposed in the cavity 34, and between the fan 50 and the cap 58. The scent capsule 58 can have a chamber containing a fragrant and/or scented material or liquid 62, and can have a substantially flat permeable membrane 66 through which a fragrance of the fragrant material can permeate over time. The fragrant material can be a liquid, such as a fragrant oil. A scented liquid, such as oil, can be colored so that it translucent to aid in visibility. The liquid or oil can also move in the chamber or vessel to aid in visibility. The permeable membrane 66 can be located adjacent the fan 50. The membrane can be in close proximity to, and directly in front of, the fan and blades thereof. The permeable membrane 66 can be substantially flat and oriented transverse, such as perpendicularly, to an axis of the motor or fan, and to a longitudinal axis of the air freshener. The membrane can face downwardly towards the fan and stem so that air from the fan is directed against the membrane. An air flow path 70 (FIG. 7b) is defined through bulbous head 30 of the housing 22, in through the bottom vent aperture 42, past the permeable membrane 66 of the scent capsule 58, and out of the top vent aperture 46. The air path can extend past lateral sides of the scent capsule and membrane. One or more gaps 72 (FIG. 6a) can be formed between the housing 22 and/or bulbous head 30 and the scent capsule 58 and/or membrane 66 to allow for the air flow. The scent capsule 58 can have a long dimension oriented transverse to a long dimension of the bulbous head to form the gaps. Thus, the scent capsule can be oblong in one direction and the housing or bulbous head can be oblong in a perpendicular direction. The scent capsule 58 can be aligned with, and disposed over or in-line with, an axis of the motor and the fan; while the bottom vent opening 42 and the top vent opening 46 are located outside a width of the scent capsule to form the gaps.

The cap 38 can include a scent capsule aperture 74 through which the scent capsule 58 can be viewed. The scent capsule 58 can include a clear dome projecting at least to the scent capsule aperture. Thus, the fragrant material 62 can be visible through the clear dome and the scent capsule aperture. Thus, the amount of scent material remaining can be ascertained. The clear dome of the scent capsule can project into the aperture 74, without extending through the aperture, or out of the cap or head. Thus, the cap or head, or a portion thereof surrounding the aperture, can protect the clear dome. In addition, lateral sides of the clear dome of the scent capsule can match the sides of the aperture, so that the clear dome has the same shape as the aperture. An outermost surface of the clear dome can match the shape and/or curvature of the cap. The outermost surface of the clear dome and the outer surface of the cap surrounding the aperture can be substantially flush. The clear dome and the lateral sides of the scent capsule can be formed by, or can form, the chamber or vessel of the scent capsule. The clear dome of the scent capsule can be formed by the vessel or chamber thereof that contains the scent material. The scent capsule can include a plastic sheet that is both indented or concave on one side, and convex or protruding on the other side. Thus, the vessel or chamber of the scent capsule can be concave or indented to receive the scent material (and covered by the membrane), while protruding or convex to form the dome.

Figure 6A:
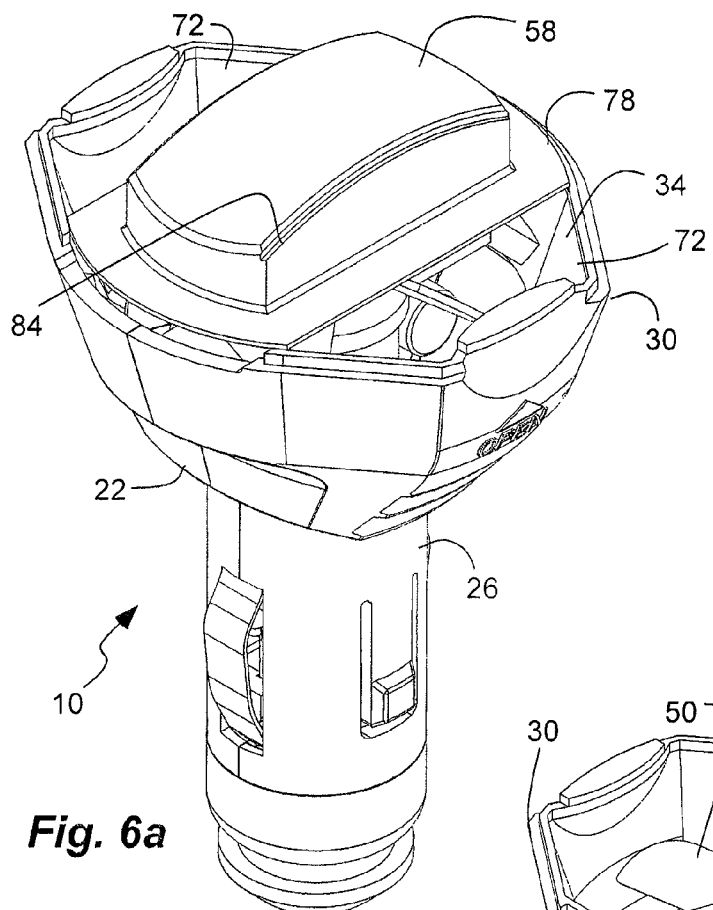
FIG. 6a is a perspective view of the air freshener of FIG. 1, with a cap removed.
Figure 6B:
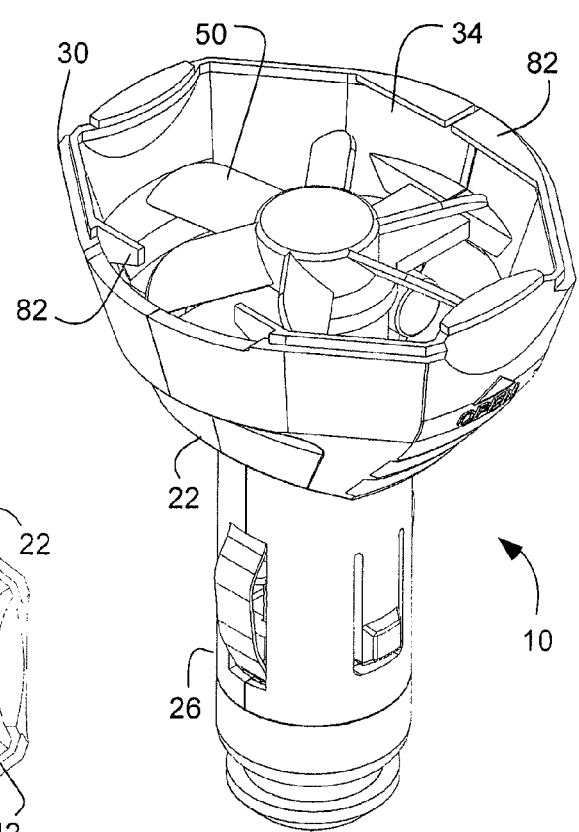
FIG. 6b is a perspective view of the air freshener of FIG. 1, with the cap and a scent capsule removed.
Figure 6C:
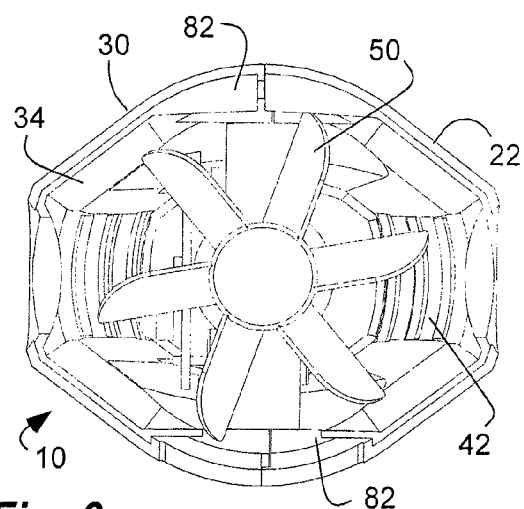
FIG. 6c is a top view of the air freshener of FIG. 1, with the cap and the scent capsule removed.
Figure 7A:
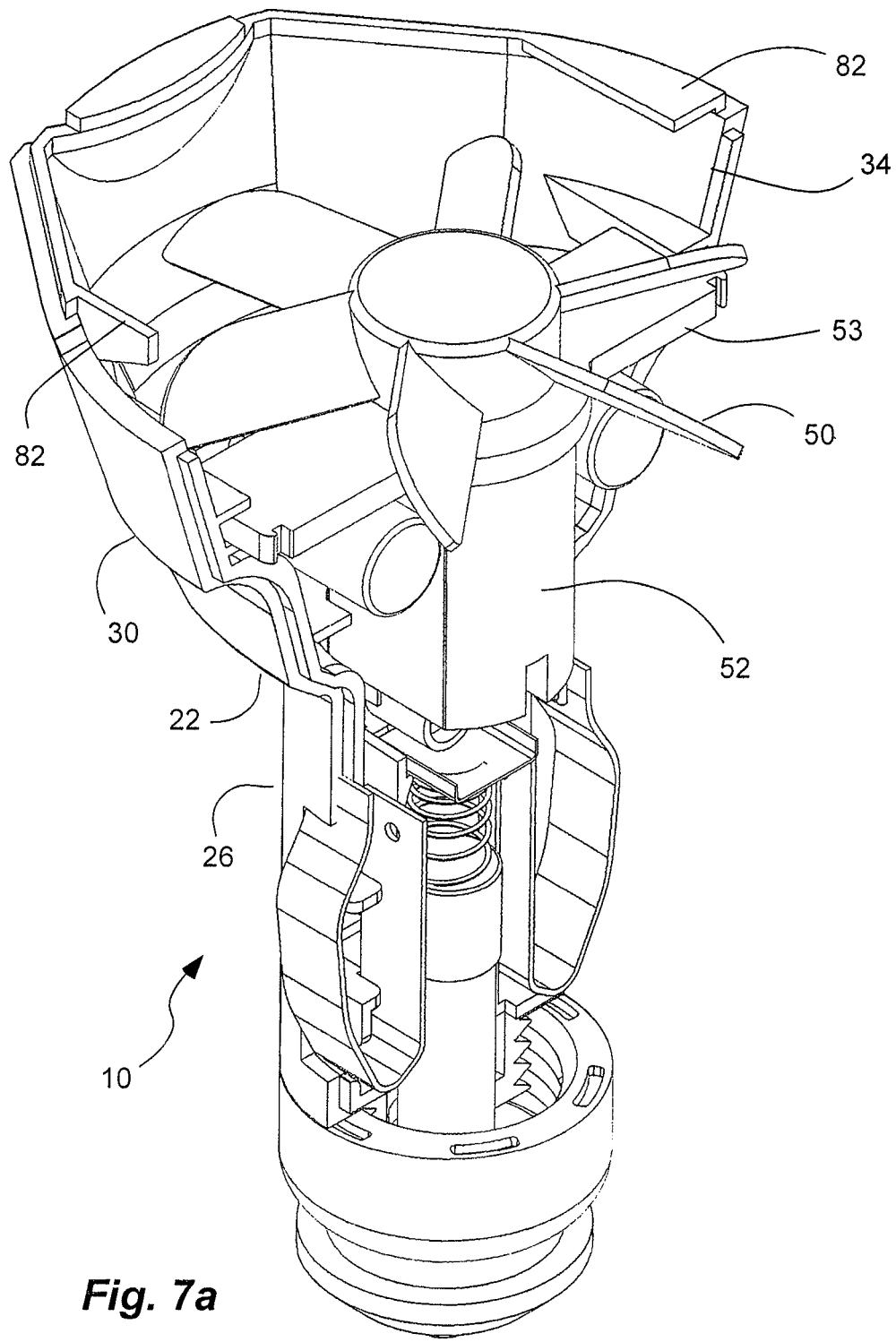
FIG. 7a is a partial cross-sectional perspective view of the air freshener of FIG. 1, with a housing half and the cap removed, and some components not cross-sectioned, such as a fan and a motor.
Figure 7B:
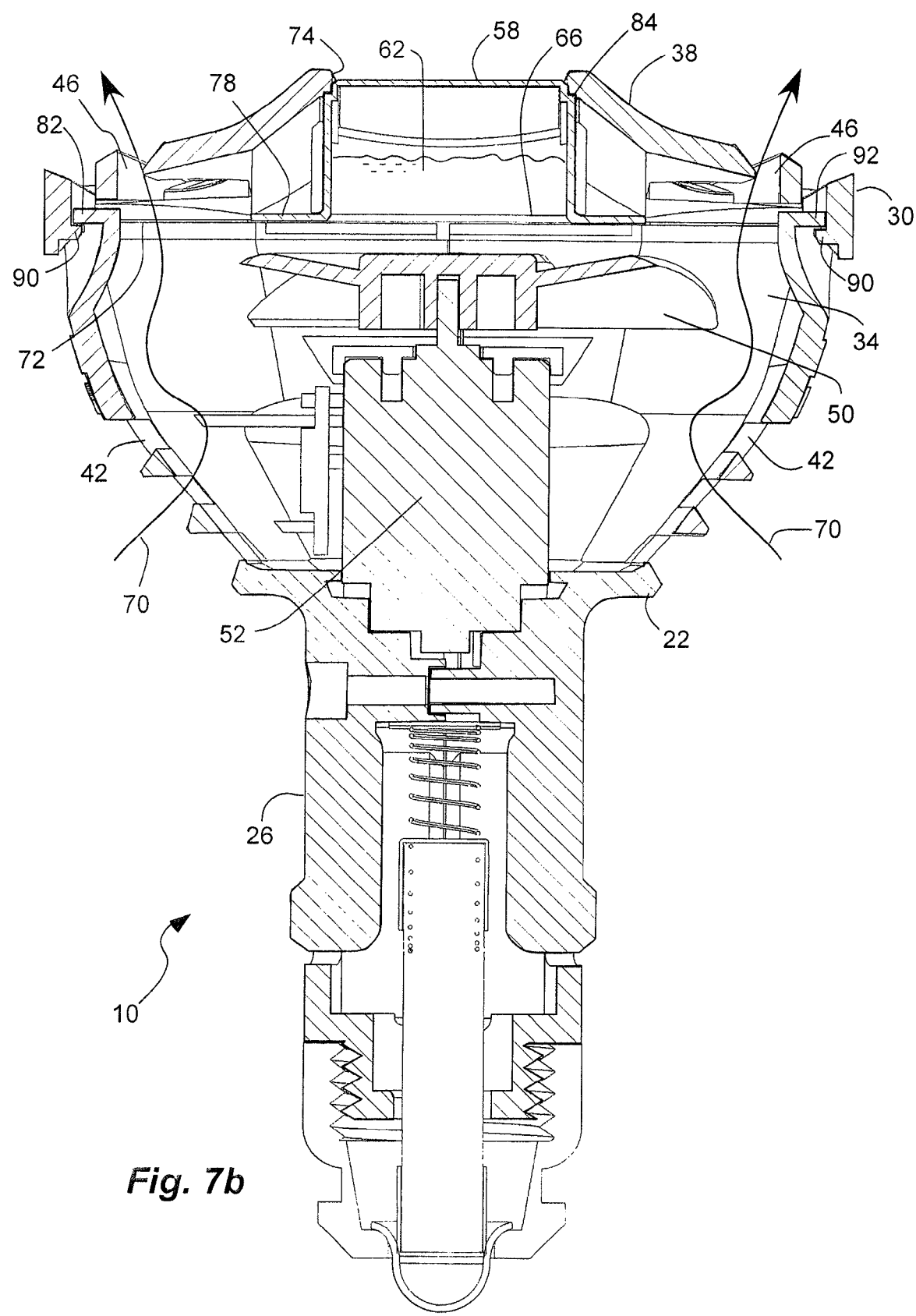
FIG. 7b is a cross-sectional side view of the air freshener of FIG. 1, taken along line 7b of FIG. 3.
Figure 7C:
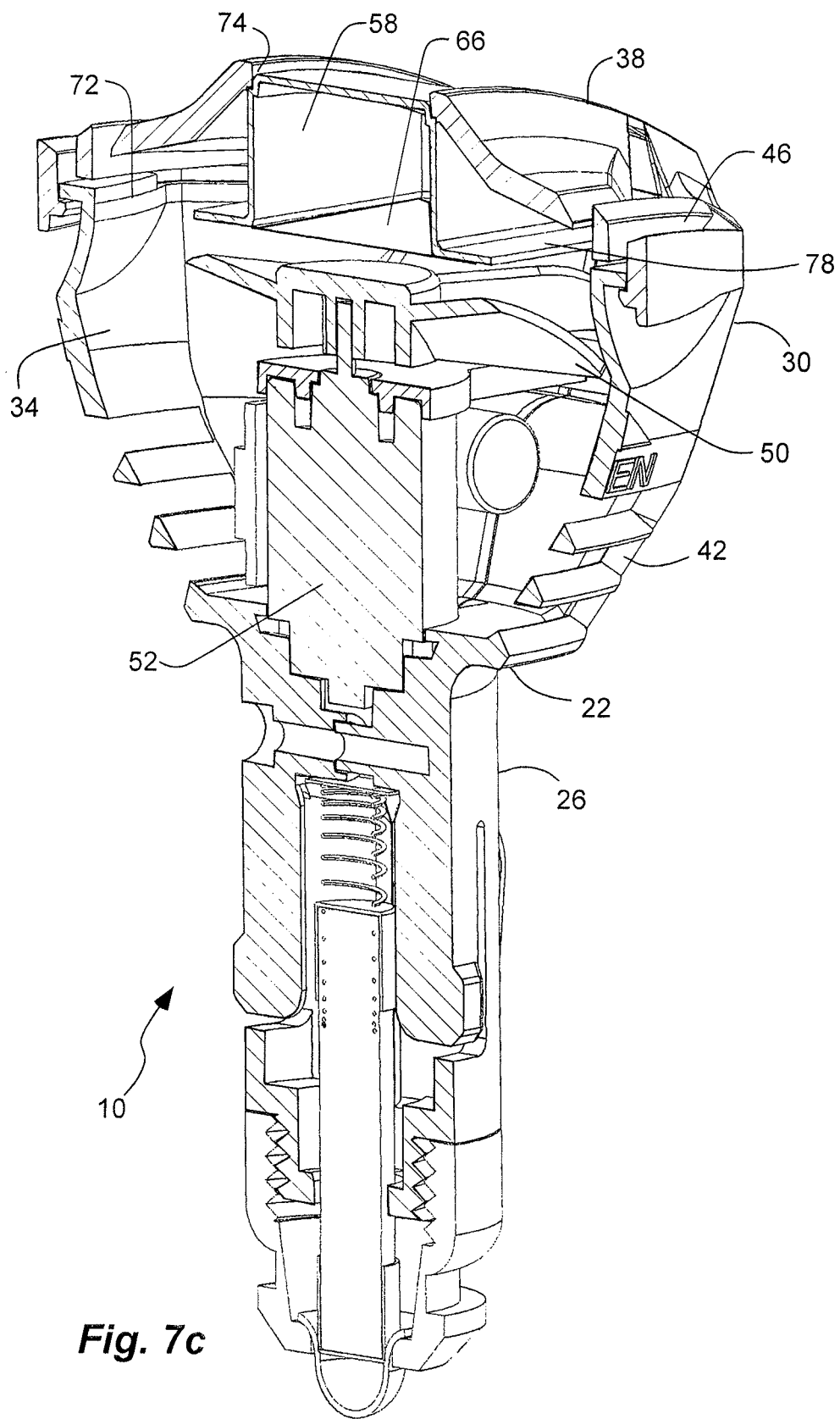
FIG. 7c is a cross-sectional perspective view of the air freshener of FIG. 1, taken along line 7b of FIG. 3.
Figure 7D:
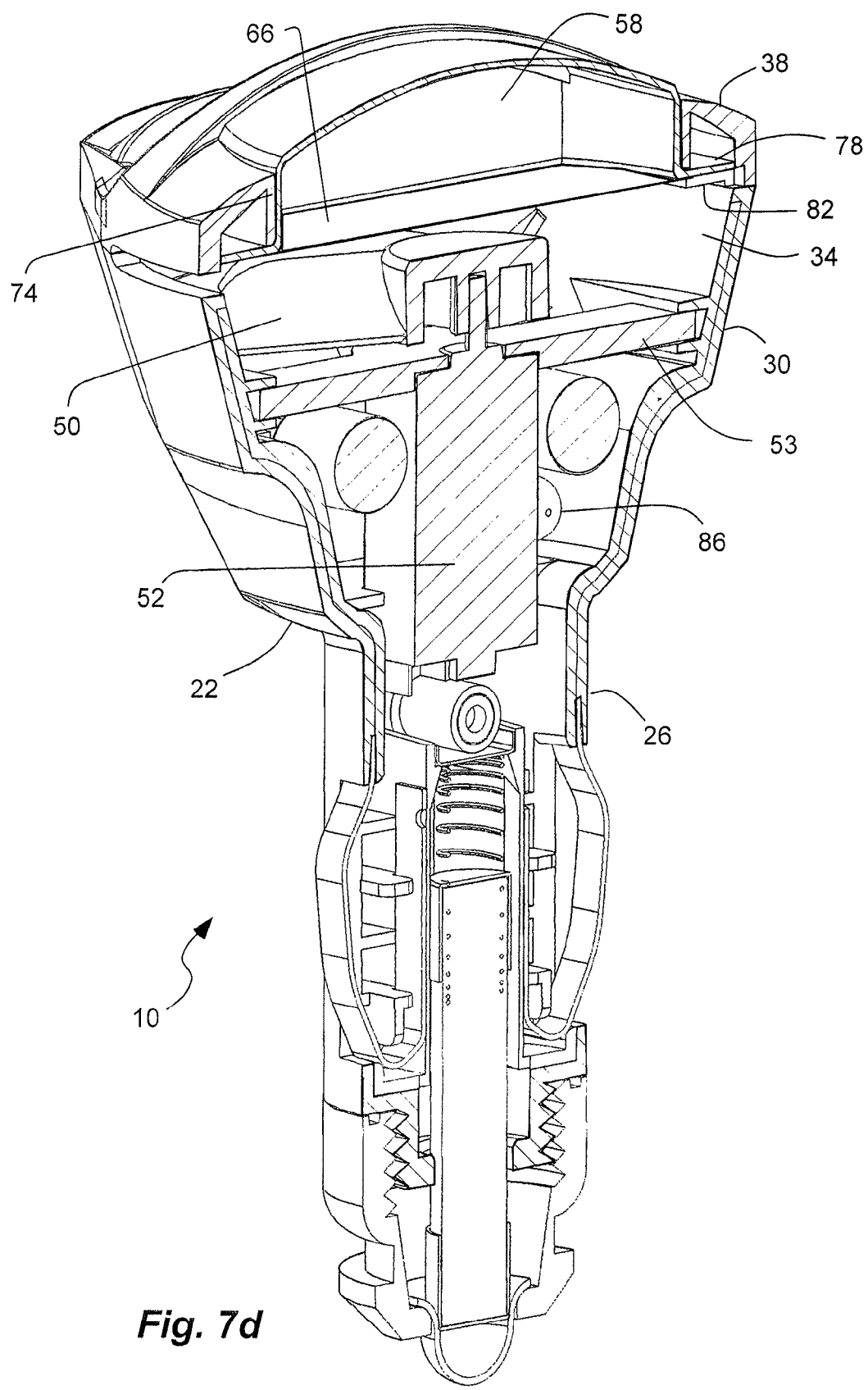
FIG. 7d is a cross-sectional perspective view of the air freshener of FIG. 1, taken along line 7d of FIG. 2.
Figure 7E:
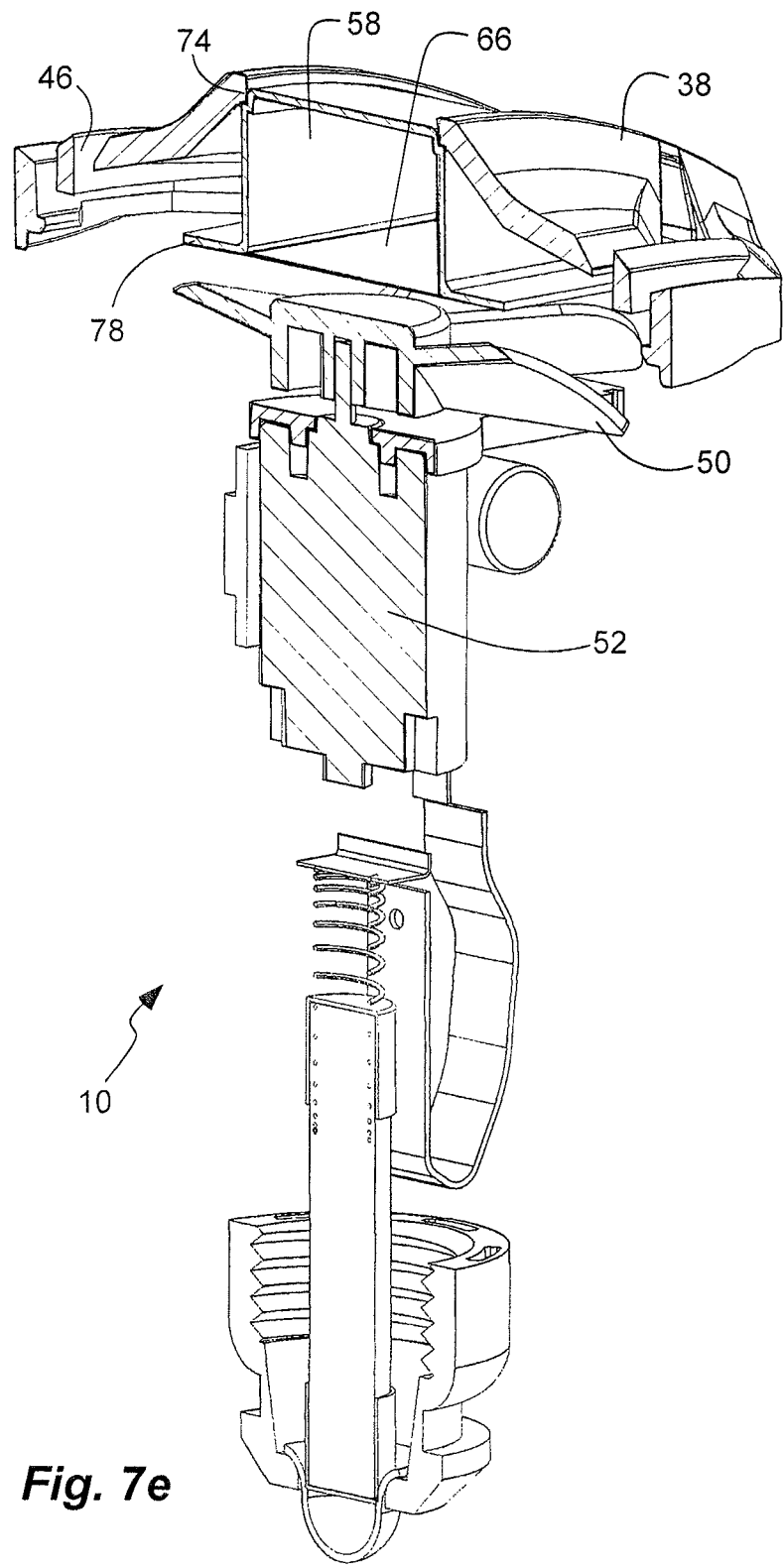
FIG. 7e is a partial cross-sectional perspective view of the air freshener of FIG. 1, taken along line 7b of FIG. 3, with all or portions of some components removed, such as a body and a stem.
Figure 8:
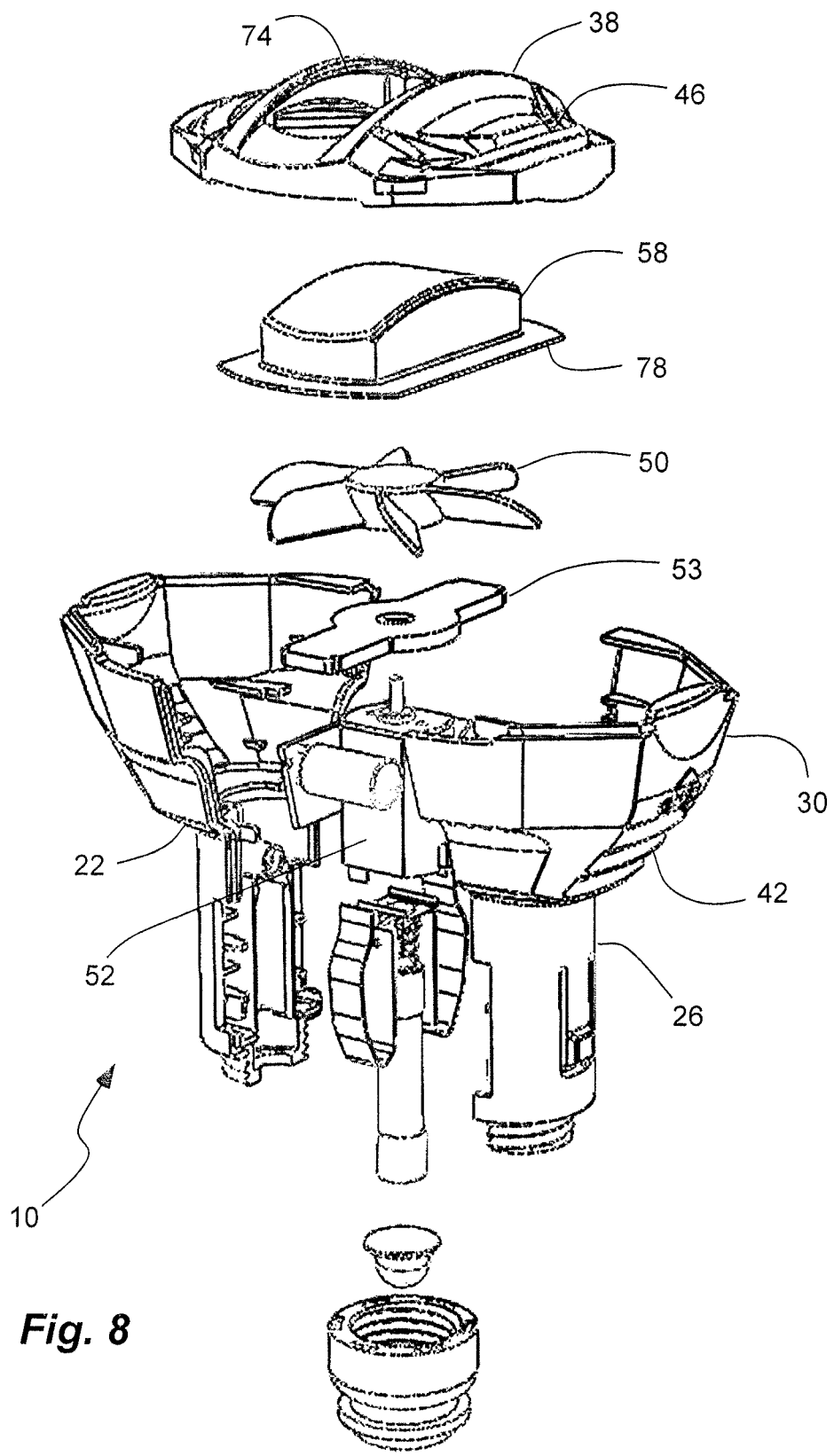
FIG. 8 is an exploded view of the air freshener of FIG. 1.
Figure 9:
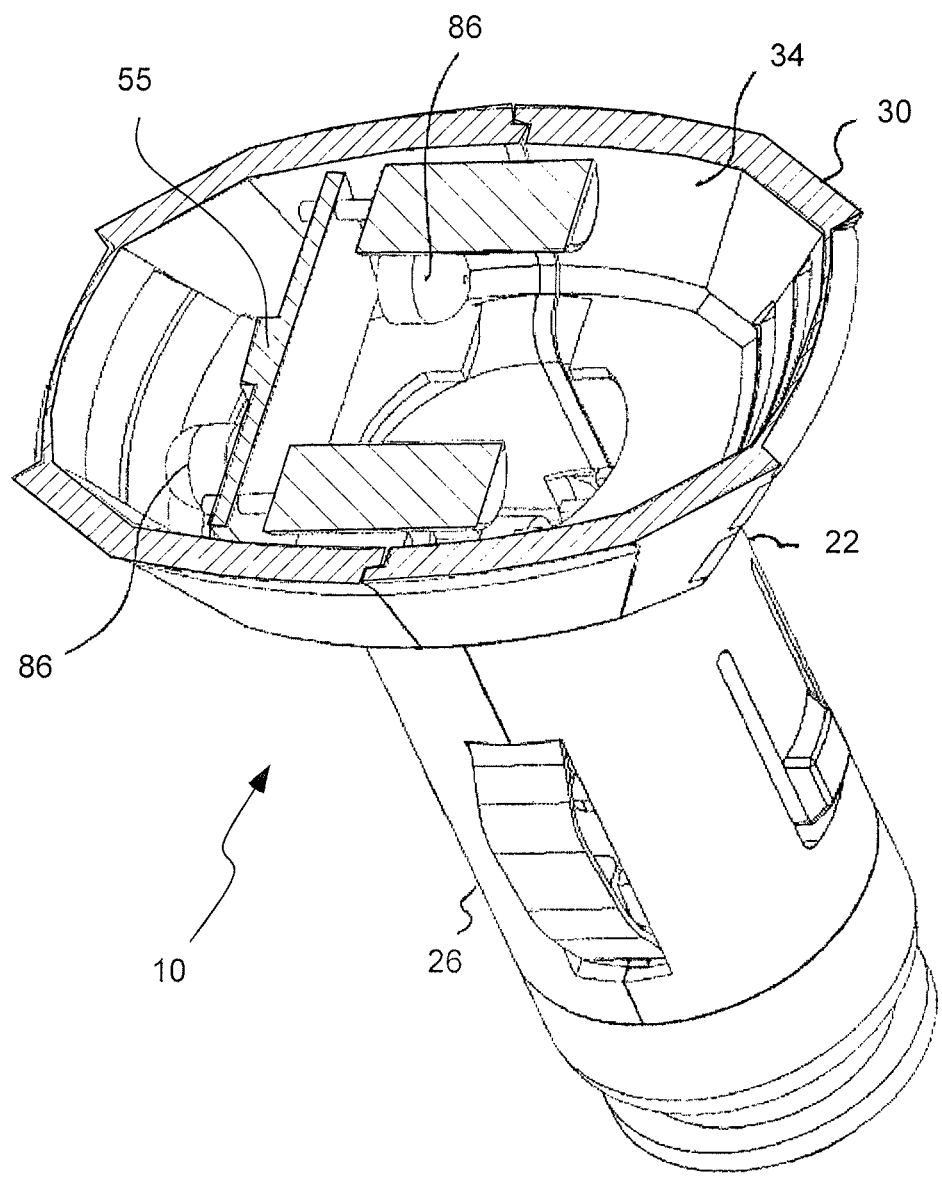
FIG. 9 is a cross-sectional perspective view of the air freshener of FIG. 1, taken along line 9 of FIG. 2, with some components removed, such as the motor.

The scent capsule can further including a perimeter flange 78 circumscribing the clear dome with a size greater than the scent capsule aperture to retain the scent capsule. In addition, the perimeter flange 78 of the scent capsule 58 can rest on the housing 22, or flanges 82 thereof, as shown in FIGS. 6a and 6b, to support the scent capsule above the fan and in the scent capsule aperture. The perimeter flange 78 can also abut to the cap. The perimeter flange 78 or portion thereof can be sandwiched between the cap and the flanges 82 of the housing. The thickness or height of the scent capsule, or dome, can be less than or equal to a depth of the aperture 74 so that a top of the scent capsule (or chamber, vessel, or dome) does not protrude through the scent capsule aperture 74, or past a top of the cap, and so that the cap 38 protects the scent capsule (or chamber, vessel or dome). Alternatively, the chamber, vessel or dome of the scent capsule can protrude from the cover, and the fragrant material or portion thereof can be disposed outside the cover, and thus the housing and body, for increased visibility. Furthermore, all or a portion of an upper and outer perimeter of the clear dome can have a step formed therein to create a shoulder 84 (FIGS. 6a and 7b) below the outermost surface of the clear dome that can abut to the cap at the aperture to maintain the clear dome aligned in the aperture and/or to resist displacement of the scent capsule out of the aperture, along with the perimeter flange.

A light source 86, such as one or more LEDs, can be disposed in the cavity 34 of the housing 22, or in the bulbous head. The light source 86 can be positioned behind the bottom vent apertures 42 to direct light out the bottom vent apertures or louvers. Thus, the air freshener can also provide an indirect light source. In addition, the membrane 66 and the scent material 62, such as the liquid, can be at least translucent, while the housing and cap can be opaque. Thus, the light source 86 disposed in the housing can also illuminate the membrane and fragrant material therein. Thus, the light from the light source can visible through the clear dome and the scent capsule aperture. The light can further assist in ascertaining the amount of scent material remaining. The light can be modified, such as change in color and/or intensity, by the membrane and/or the scent material. In addition, the clear dome, or outermost surface thereof, of the scent capsule can include indicia thereon that can be more opaque than the clear dome and/or scent material, so that it is highlighted by the light source. Alternatively, indicia can be disposed on the membrane. Furthermore, light can be directed through the top vent apertures 46.

The cap 38 can have opposite tabs 90 that project inward and engage opposite tabs 92 on the housing to retain the cap on the housing. The housing 22 can be flexible and resilient, such that pressing inwardly on the housing can disengage the tabs so that the cap can be removed from the housing, and the scent capsule removed and replaced.

A slot can be formed in the housing adjacent the membrane. A release liner can be removably coupled over the membrane, with a tab extending through the slot. The tab can be grasped and removed from the membrane and the housing.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. An air freshener device configured to be carried by a power outlet of an automobile, the device comprising:
   a) a housing with a stem and a head with a cavity therein, the stem sized and shaped to be inserted into the power outlet of the automobile;
   b) an air displacement mechanism carried by the housing including a rotatable fan carried by the head, and a motor coupled to the fan to rotate the fan; and
   c) a scent capsule removably carried by the head and having a chamber containing a fragrant material and having a permeable membrane through which a fragrance of the fragrant material can permeate over time, the permeable membrane located adjacent the fan.

2. A device in accordance with claim 1, wherein the housing has an air flow path defined through the housing in through a bottom vent aperture, past the permeable membrane of the scent capsule, and out of a top vent aperture.

3. A device in accordance with claim 2, further comprising:
a cap disposed on the housing and forming a portion of the head and the cavity, with the top vent aperture formed in the cap.

4. A device in accordance with claim 1, wherein the head includes a scent capsule aperture and the scent capsule includes a clear dome projecting to at least the scent capsule aperture with the fragrant material visible through the clear dome and the scent capsule aperture.

5. A device in accordance with claim 4, wherein the membrane is at least translucent; and further comprising a light source disposed in the housing to illuminate the membrane and fragrant material therein such that light from the light source is visible through the clear dome and the scent capsule aperture.

6. A device in accordance with claim 1, wherein the air displacement mechanism further includes a switch coupled to the motor to selectively activate and deactivate the air displacement mechanism.

7. A device in accordance with claim 6, further comprising:
a timer circuit coupled to the switch to deactivate the fan after a predetermined amount of time.

8. A device in accordance with claim 1, wherein an axis of the fan is oriented transverse to the permeable membrane of the scent capsule.

9. A device in accordance with claim 1, wherein the scent capsule forms a vessel covered by the permeable membrane and wherein the fragrant material is a liquid contained within the vessel with the permeable membrane facing downwardly towards the steam.

10. A device in accordance with claim 1, wherein the scent capsule has a long dimension oriented transverse to a long dimension of the head.

11. A device in accordance with claim 1, wherein the scent capsule is aligned with an axis of the motor and the fan; and wherein a bottom vent opening and a top vent opening are located outside a width of the scent capsule.

12. A device in accordance with claim 1, further comprising:
a light source in the housing and positioned to direct light out a bottom vent aperture.

13. An air freshener device in combination with a power outlet of an automobile, the device comprising:
a) a housing with a stem and a bulbous head with a cavity therein, the stem sized and shaped to be inserted into the power outlet of the automobile, and including a pair of terminals thereon capable of contacting mating terminals in the power outlet;
b) a cap disposed on the housing and forming a portion of the bulbous head and the cavity;
c) the bulbous head having a bottom vent aperture in a bottom and a top vent aperture in a top or the cap;
d) an air displacement mechanism carried by the housing including a rotatable fan carried by the bulbous head, a motor coupled to the fan to rotate the fan, the motor coupled to the pair of terminals to power the motor;
e) a scent capsule removably carried by the bulbous head and having a chamber containing a fragrant material and having a substantially flat permeable membrane through which a fragrance of the fragrant material can permeate over time, the permeable membrane located adjacent the fan;
f) an air flow path defined through bulbous head of the housing in through the bottom vent aperture, past the permeable membrane of the scent capsule, and out of the top vent aperture; and
g) the cap including a scent capsule aperture and the scent capsule including a clear dome projecting at least to the scent capsule aperture with the fragrant material visible through the clear dome and the scent capsule aperture.

14. A device in accordance with claim 13, wherein the membrane is at least translucent; and further comprising a light source disposed in the housing to illuminate the membrane and fragrant material therein such that light from the light source is visible through the clear dome and the scent capsule aperture.

15. A device in accordance with claim 13, wherein an axis of the fan is oriented perpendicularly to the substantially flat permeable membrane of the scent capsule.

16. A device in accordance with claim 13, wherein the scent capsule forms a vessel covered by the permeable membrane and wherein the fragrant material is a liquid contained within the vessel with the permeable membrane facing downwardly towards the stem.

17. A device in accordance with claim 13, wherein the scent capsule has a long dimension oriented transverse to a long dimension of the bulbous head.

18. A device in accordance with claim 13, wherein the scent capsule is aligned with an axis of the motor and the fan; and wherein the bottom vent opening and the top vent opening are located outside a width of the scent capsule.

19. A device in accordance with claim 13, further comprising:
a light source in the housing and positioned to direct light out the bottom vent aperture.

20. An air freshener device configured to be carried by a power outlet of an automobile, the device comprising:
a) a housing with a stem and a bulbous head with a cavity therein, the stem sized and shaped to be inserted into the power outlet of the automobile, and including a pair of terminals thereon capable of contacting mating terminals in the power outlet;
b) a cap disposed on the housing and forming a portion of the bulbous head and the cavity;
c) the bulbous head having a bottom vent aperture in a bottom and a top vent aperture in a top or the cap;
d) an air displacement mechanism carried by the housing including a rotatable fan carried by the bulbous head, a motor coupled to the fan to rotate the fan, the motor coupled to the pair of terminals to power the motor;
e) a scent capsule removably carried by the bulbous head and having a vessel containing a fragrant liquid and covered by a substantially flat permeable membrane through which a fragrance of the fragrant liquid can permeate over time, the permeable membrane located adjacent to and facing towards the fan and oriented perpendicular to an axis of the fan;
f) the scent capsule having a long dimension oriented transverse to a long dimension of the head with the bottom vent opening and the top vent opening located outside a width of the scent capsule and having an air flow path defined through bulbous head of the housing in through the bottom vent aperture, past the permeable membrane of the scent capsule, and out of the top vent aperture;
g) a scent capsule aperture formed in the cap;
h) a clear dome of the scent capsule projecting at least to the scent capsule aperture with the fragrant liquid visible through the clear dome and the scent capsule aperture;

i) the membrane being at least translucent; and
j) a light source disposed in the housing to illuminate the membrane and fragrant liquid therein such that light from the light source is visible through the clear dome and the scent capsule aperture.

\* \* \* \* \*